(12) United States Patent
Zepf

(10) Patent No.: US 7,556,499 B2
(45) Date of Patent: Jul. 7, 2009

(54) DENTAL FORCEPS

(75) Inventor: Helmut Zepf, Seitingen-Oberflacht (DE)

(73) Assignee: Helmut Zepf Medizintechnik GmbH, Seitingen-Oberflacht (DE)

(*) Notice: Subject to any disclaimer, the term of this patent is extended or adjusted under 35 U.S.C. 154(b) by 0 days.

(21) Appl. No.: 11/399,472

(22) Filed: Apr. 7, 2006

(65) Prior Publication Data
US 2006/0228670 A1 Oct. 12, 2006

(30) Foreign Application Priority Data
Apr. 11, 2005 (DE) .................. 20 2005 005 722 U

(51) Int. Cl.
*A61C 3/14* (2006.01)
(52) U.S. Cl. ................ 433/159; 433/4; 606/207; 81/424.5
(58) Field of Classification Search ............... 433/159, 433/157, 160, 156, 161, 4; D24/153; 606/207; 81/418, 420, 424.5, 426, 426.5, 3.6
See application file for complete search history.

(56) References Cited

U.S. PATENT DOCUMENTS

| 97,399 | A | * | 11/1869 | Holmes | 294/118 |
|---|---|---|---|---|---|
| 165,808 | A | * | 7/1875 | Durham | 433/146 |
| 214,104 | A | * | 4/1879 | Cobb | 433/159 |
| 292,643 | A | * | 1/1884 | Friend | 81/424.5 |
| 491,515 | A | * | 2/1893 | Blake | 433/159 |
| 649,742 | A | * | 5/1900 | Mories | 433/159 |
| 682,597 | A | * | 9/1901 | Bennett | 433/159 |
| 731,586 | A | * | 6/1903 | Manning | 433/159 |
| 991,313 | A | * | 5/1911 | Hull | 433/159 |
| 1,116,093 | A | * | 11/1914 | McKaig | 7/134 |
| 1,626,226 | A | * | 4/1927 | Cantor | 433/159 |
| 1,661,365 | A | * | 3/1928 | Gendron | 29/248 |
| 1,740,591 | A | * | 12/1929 | Harter | 81/426.5 |
| 1,753,080 | A | * | 4/1930 | Zwilling et al. | 81/3.6 |
| 2,497,229 | A | | 2/1950 | Mollner | |
| 2,504,227 | A | * | 4/1950 | Rubba | 433/159 |
| 2,674,800 | A | * | 4/1954 | Osborne et al. | 433/159 |
| 2,814,963 | A | * | 12/1957 | Harrington | 294/118 |
| 2,842,997 | A | * | 7/1958 | Wentling | 81/418 |
| 2,847,889 | A | * | 8/1958 | Cain | 81/424.5 |

(Continued)

FOREIGN PATENT DOCUMENTS

CH 293 561 12/1953
DE 85 12 734.5 10/1985

*Primary Examiner*—Ralph A Lewis
(74) *Attorney, Agent, or Firm*—The Nath Law Group; Jerald L. Meyer; Sungyeop Chung

(57) ABSTRACT

The invention relates to a dental forceps with two articulated parts, which are connected to each other at a pivot and which each exhibit a handle at one end and at the other end a working end with an inside area, such that the inside area exhibits a corrugated area which runs perpendicular to the longitudinal axis, and such that a longitudinal groove is positioned within the inside area, starting at the distal end of the working end and running along the longitudinal axis of the working end, and such that a recessed cavity is positioned in the longitudinal groove, starting at the distal end, and the radius of curvature of the recessed cavity is smaller than the radius of curvature of the longitudinal groove.

12 Claims, 4 Drawing Sheets

U.S. PATENT DOCUMENTS 3,017,692 A * 1/1962 Burnell .......................... 29/229
3,270,745 A * 9/1966 Wood .......................... 606/158
5,044,954 A * 9/1991 Lukase et al. ............... 433/159
5,855,048 A * 1/1999 Synowicki et al. ............. 29/10
2003/0233915 A1* 12/2003 Takasaki .................... 81/424.5

* cited by examiner

DENTAL FORCEPS

FIELD OF THE INVENTION

The invention relates to a dental forceps.

BACKGROUND

The prior art is acquainted with dental forceps exhibiting two articulated parts, which are connected to each other at a pivot. Here each articulated part exhibits a handle at one end and at the other a working end with an inner area and an outer area. The inner area exhibits a corrugated portion running across the longitudinal axis, and this corrugated portion makes it easier to grip the teeth with the forceps. In the inside area, proceeding from the distal end of the working end, the known dental forceps also exhibit a longitudinal groove running along the longitudinal axis of the working end; the longitudinal groove has a radius of curvature which is comparatively large, with the result that the longitudinal groove is bent concavely to only slight degree and is almost flat. When a tooth is grasped with the dental forceps, the recessed cavity does not completely encompass the tooth, but instead the tooth is gripped by the flat longitudinal groove at certain points only. In the process of luxation this results in a riding movement during which the tooth does not lie smoothly in the dental forceps. In the process of luxation this riding movement can bring about damage to the tooth, particularly fractures to the crown and root.

SUMMARY

The goal of the invention therefore consists in providing a dental forceps which permits a more gentle process of luxation. The goal particularly consists in providing a dental forceps in which the tooth will rest evenly and damage during the process of luxation is prevented.

A goal of the invention is solved by a dental forceps exhibiting characterizing features as described below.

Advantageous embodiments and elaborations of the invention are indicated in the following descriptions.

The dental forceps according to the invention is so designed that proceeding from the distal end a recessed cavity is positioned in the longitudinal groove, at least by way of sections. The recessed cavity has a radius of curvature that is smaller than the longitudinal groove's radius of curvature. Due to its smaller radius of curvature this recessed cavity has a shape that permits its inner surface to rest smoothly on the convexly shaped outer surface of the teeth. As a result there is not just a punctuated or point-by-point contact surface between the dental forceps and tooth, but an even one, which provides an improved degree of contact between the dental forceps and the tooth, with the result that the tooth is held firmly during the luxating movement, and a riding motion is avoided.

In an advantageous elaboration of the invention the radius of curvature of the recessed cavity approximates the radius of curvature of the tooth. The inner surface of the dental forceps is designed to accommodate the anatomical conditions of the teeth. In particular, the concave shape of the recessed cavity corresponds to the convex shape of the crown of the tooth being pulled, with the result that there is optimal contact between the dental forceps and the tooth. This permits a more gentle process of luxation.

The recessed cavity may extend over the entire length of the longitudinal groove. Ideally, however, the recessed cavity will occupy only about a third of the length of the longitudinal groove. Thus the recessed cavity does not extend over the entire length of the working end of the dental forceps, as this is not necessary, since as a rule the tooth being extracted is seized only with the front third of the working end of the forceps.

Ideally the recessed cavity will exhibit an ellipsoidal transitional area leading to the longitudinal groove, thus eliminating sharp edges and transitional areas that might damage the tooth being extracted.

In a particularly preferred embodiment of the invention the width of the recessed cavity will approximate the width of the tooth. The recessed cavity thus encloses the tooth entirely and thereby assures a particularly good degree of contact between the forceps and the tooth. In order to accommodate the differing size of teeth—such as incisors, premolars, molars, and wisdom teeth—a plurality of dental forceps can be produced, in which the recesses have different widths corresponding to the different average sizes of the teeth.

In an advantageous elaboration of the invention the longitudinal edges of the recessed cavity have a cylindrically ground surface. During the turning movements around the longitudinal axis of the tooth, which are customarily executed in the process of luxation, the cylindrically ground surface engages with the tooth and thereby additionally assures that the tooth has a secure seat in the dental forceps.

Ideally the indentations or teeth of the cylindrically ground surface will have a spacing of about 1 mm. This distance is greater than the otherwise customary spacing of indentations in a corrugated area; the result is that the indentations may additionally engage with the tooth and facilitate the luxation process.

The ground surface on the rim of the recessed cavity will ideally extend into the recessed cavity itself. This eliminates a transitional area with sharp edges, which might damage the teeth unnecessarily and cause fractures. Concurrently the indentations in the ground surface engage that much more quickly and certainly during the turning movements around the longitudinal axis of the teeth, and the result is that the tooth is provided an even more secure position in the dental forceps.

In a particularly preferred embodiment of the invention the dental forceps is designed as a stump forceps. Accordingly the recessed cavity is particularly narrow, e.g., only about 2 mm wide. Given this condition, the working end itself can have a very slender design. This kind of dental forceps allows broken root apexes, sequestra, or other foreign bodies to be safely removed from the alveolus, with damage to the alveolus.

The working end will ideally be bent 45 to 90 degrees away from the longitudinal axis of the articulated parts. This permits the dental forceps to be more simply introduced into the oral cavity and assures better access to the tooth being extracted, or to root apexes or dental splinters being removed.

BRIEF DESCRIPTION OF THE DRAWINGS

An exemplary embodiment of the invention is next explained in detail on the basis of the following figures, which show.

DETAILED DESCRIPTION OF THE DRAWINGS

Figure 1:
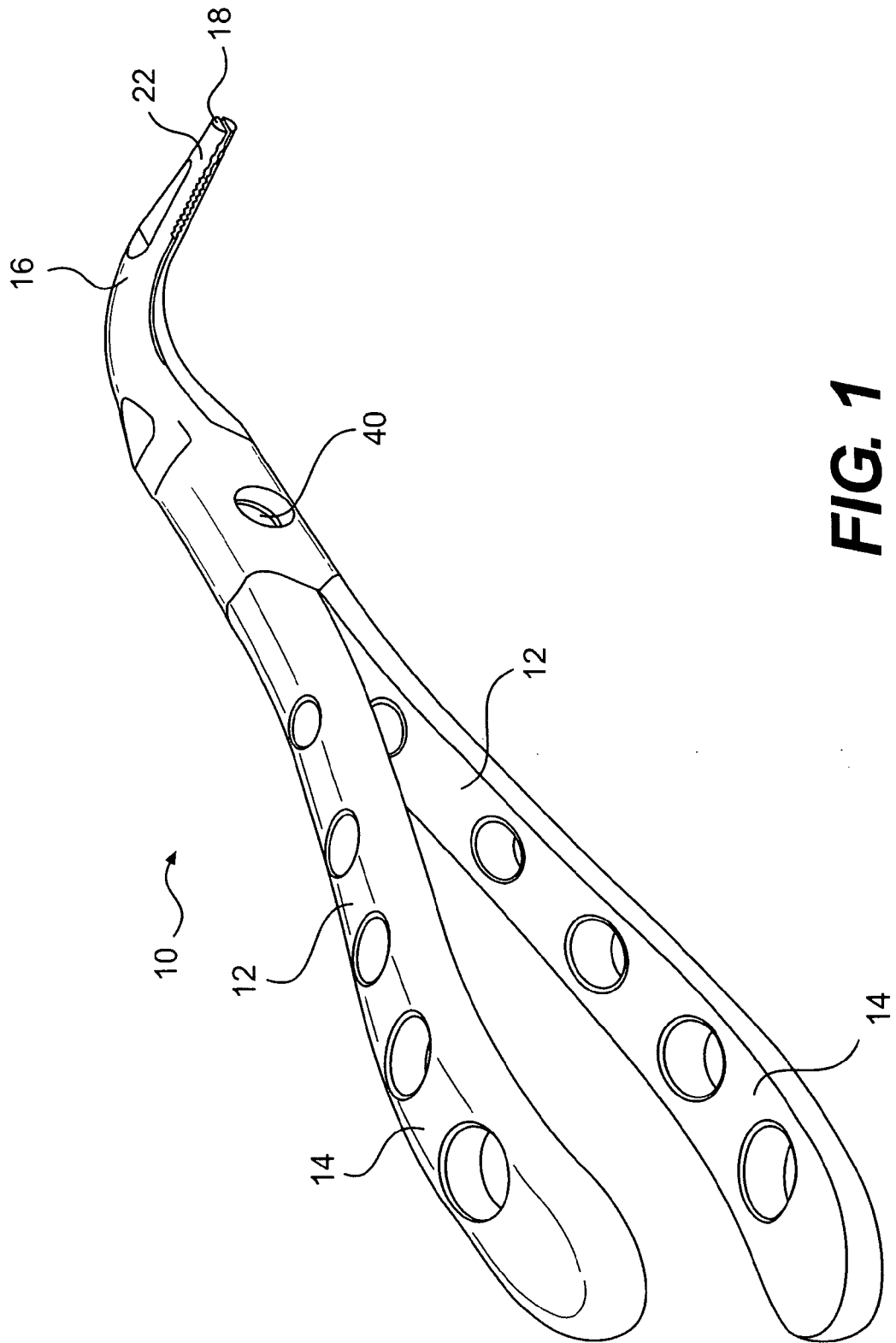
FIG. 1 a perspective view of an exemplary embodiment of the dental forceps according to the invention FIG. 2 a top view of the dental forceps of FIG. 1
Figure 2:
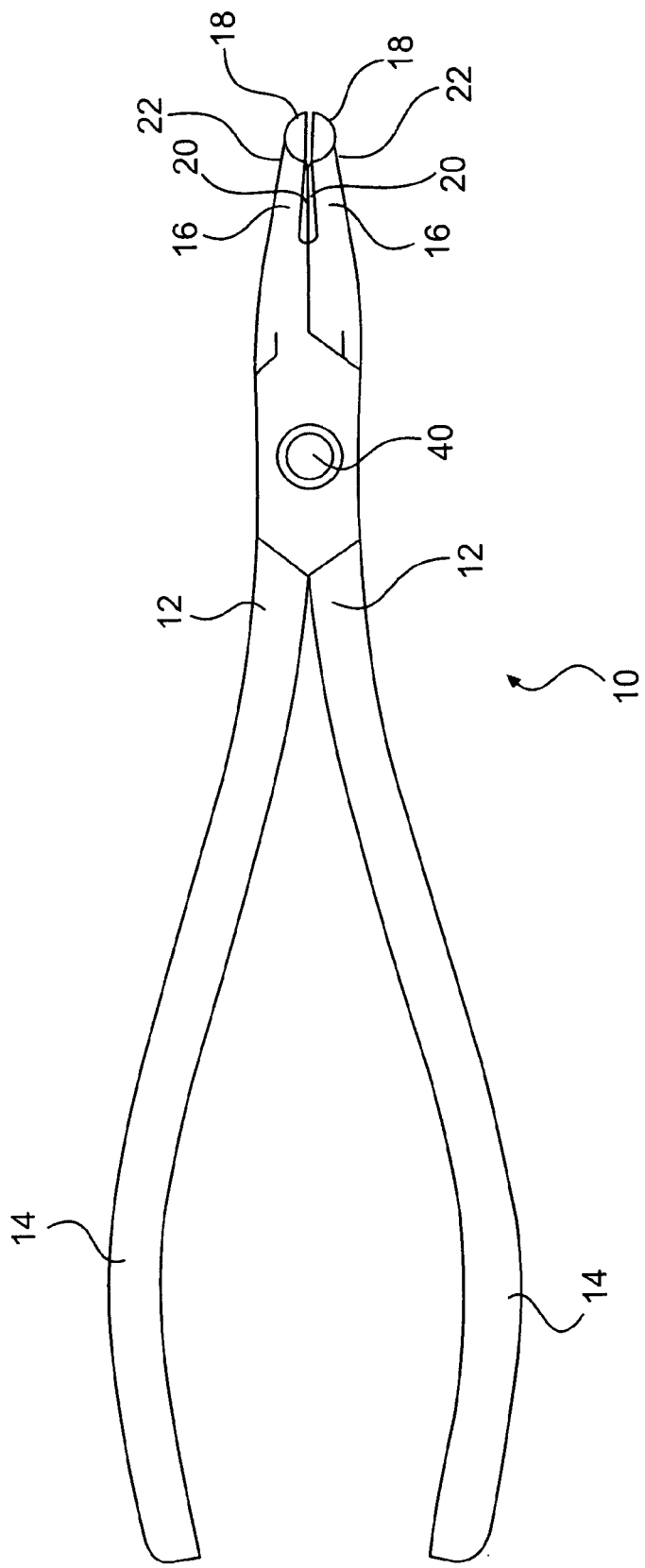

FIG. 1 provides a perspective view and FIG. 2 a top view of an exemplary embodiment of the inventive dental forceps 10, with two articulated parts 12, which are connected at a pivot 40. Each of the two articulated parts 12 has a handle 14 at one end, and at the other end a working end 16, which exhibits a distal end 18, an inside area 20, which rests on the inside area 20 of the other articulated part when the dental forceps 10 is closed, and an outside area 22.

Figure 3:
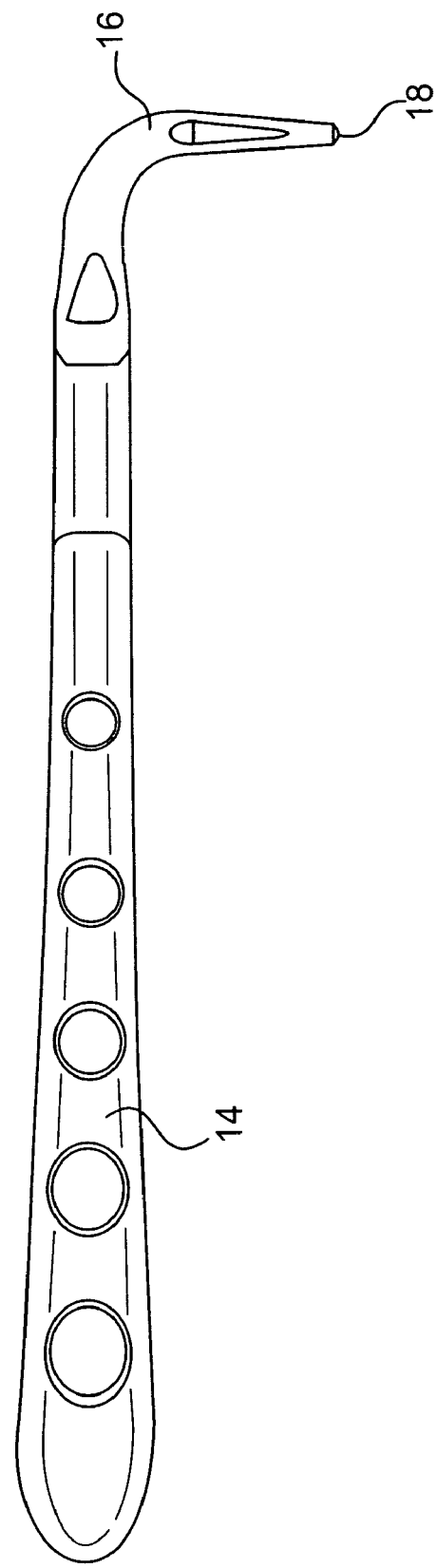
FIG. 3 a side view of the dental forceps of FIG. 1

FIG. 3 provides a side view of one of the articulated parts 12 of the same inventive dental forceps 10 shown in FIGS. 1 and 2. Here it can be clearly seen that the working end 16 is bent at angle of about 90 degrees from the longitudinal axis of the articulated part 12. This design of the working end 16 assures that there is better access to the tooth being extracted, or to splinters, e.g., root apexes, that must be removed, as well as to other foreign bodies, particularly in the alveolus.

Figure 4:
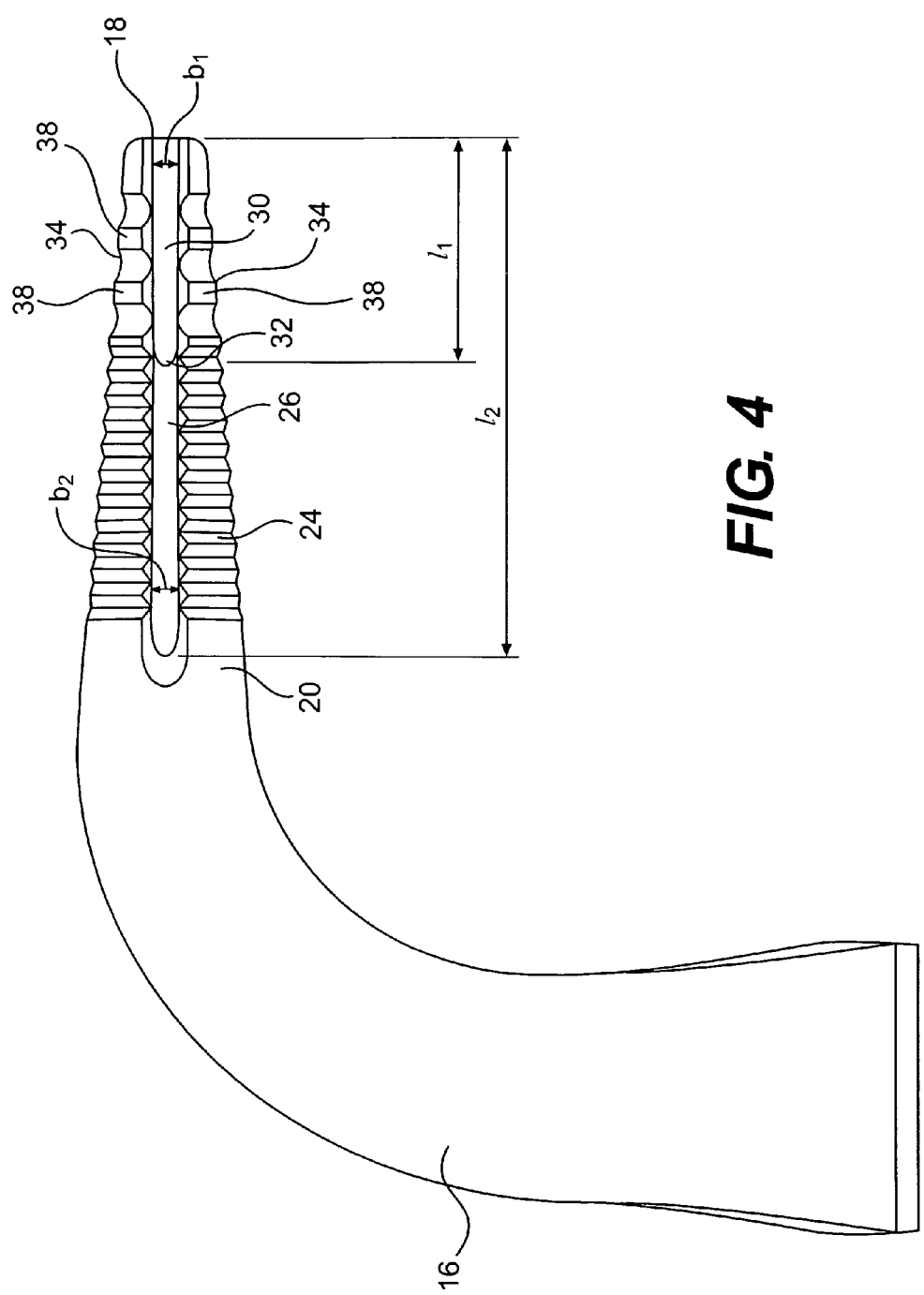
FIG. 4 a top view of the inside area of the working end of an articulated portion of the dental forceps of FIG. 1

FIG. 4 gives a top view of the inside area 20 of the working end 16 of one of the two articulated parts 12 of the dental forceps 10 according to the invention, where the working ends 16 of the two articulated parts 12 are symmetrical in design. Applied to the inside area 20 of the working end 16, and proceeding from the distal end 18, is a longitudinal groove 26, which runs along the longitudinal axis of the working end 16 and which has a length $l_2$ and a width $b_2$. This longitudinal groove has a radius of curvature which ensures that the longitudinal groove is only slightly concave and, in effect, almost flat.

Applied to the longitudinal groove 26, and proceeding from the distal end 16, is a recessed cavity 30, which has a radius of curvature that is smaller than the radius of curvature of the longitudinal groove 26. Here the radius of curvature of the recessed cavity 30 will preferably correspond to the curvature of the outer surface of the tooth to be extracted, so that the tooth will rest evenly in the recessed cavity, thereby insuring optimal contact between the inner surface of the recessed cavity 30 and the outer surface of the tooth. As a rule, the contact between the recessed cavity 30 and the tooth is sufficient for the tooth to be extracted. In the process of luxation, during which the tooth is rotated with the dental forceps around its longitudinal axis and tipped toward the cheeks or the gums, and is finally removed from the alveolus along its longitudinal axis, the tooth is held firmly in the dental forceps, with the result that riding movements between the tooth and the dental forceps are avoided. Such movements might result in damage to the tooth.

The recessed cavity 30 has a length $l_1$ and a width $b_1$. In principle the recessed cavity 30 may extend over the entire length $l_2$ of the longitudinal groove. As a rule, however, this is not necessary, since the tooth being extracted is seized with only the forward third of the working end 16 and it suffices if the longitudinal groove 26 is equipped with the recessed cavity 30 over a given section alone and if the length $l_1$ of the recessed cavity 30 is only about a third of the length $l_2$ of the longitudinal groove 26. The width $b_1$ of the recessed cavity 30 is approximately equal to the width $b_2$ of the longitudinal groove 26.

The width $b_1$ will preferably be coordinated with the width of the tooth. In order to accommodate the differing sizes of the various teeth—e.g., incisors, premolars, molars, and wisdom teeth—a plurality of inventive dental forceps 10 with differing widths $b_1$ can be held ready. Dental forceps 10 can be supplied which correspond to the average width of the teeth, with widths $b_1$ in the range from about 3 mm to 7 mm. FIGS. 1 to 4 depict an embodiment of the dental forceps 10 which is particularly preferred in this regard, one designed as a stump and splinter forceps. To this end, the width $b_1$ of the recessed cavity 30 is particularly narrow and equals only about 2 mm. Because the design of the recessed cavity 30, which is coordinated with the anatomical shape of the teeth and roots, already guarantees sufficient contact with the root or splinters, the further shape of the working end 16 can be particularly slender and narrow, with the result that it is possible in simple fashion to introduce the working end 16 of the stump and splinter forceps into the oral cavity, and particularly into the alveolus, without injury to the alveolus.

The recessed cavity 30 exhibits a transitional area 32, somewhat ellipsoid in shape, which leads to the longitudinal groove 26, with the result that sharp edges, which might damage the tooth during the process of luxation, are avoided.

The recessed cavity 30 has longitudinal edges 34, into which is set a cylindrically ground surface with indentations or teeth 38. As a result of this surface, when the forceps 10 holding the tooth is rotated around the longitudinal axis of the tooth the indentations 38 engage with the tooth and guarantee a secure grip during the rotating motions involved in the process of luxation. In an undepicted embodiment of the dental forceps according to the invention the ground surface on the rim of the recessed cavity 30 extends into the recessed cavity 30. This eliminates sharps edges and sharp transitional areas, which could bring about damage to the tooth being extracted. As a further result, the indentations 38 of the ground surface engage earlier with the tooth during the turning movements involved in the process of luxation, and provide a more secure grip on the tooth held in the recessed cavity 30. The advantage applies during all movements of the luxation process.

Proceeding from the distal end 18 of the working end 16, the ground surface runs only over roughly the length ($l_1$) of the recessed cavity 30. The distance between the indentations 38 equals about 1 mm, so that about two to four indentations 38 are positioned along the length $l_1$ of the recessed cavity 30. The comparatively large distance between the indentations 38 permits the indentations 38 to engage with, or below, the tooth during luxation, thereby facilitating the process.

Adjoining the ground surface is a corrugated area 24, which runs along the further length $l_2$ of the longitudinal groove 26 on the inside area 20 of the working end 16, and at a right angle to the longitudinal groove 26. The teeth of this corrugated area have a smaller spacing than that of the indentations 38 in the ground surface.

List of Reference Numerals 10 dental forceps
12 articulated part
14 handle
16 working end
18 distal end
20 inside area
22 outside area
24 corrugated area
26 longitudinal groove
30 recessed cavity
32 transitional area
34 longitudinal edge
38 indentations
$l_1$ length of recessed cavity
$l_2$ length of longitudinal groove
$b_1$ width of recessed cavity
$b_2$ width of longitudinal groove Invention claimed is:

1. A dental forceps (10) with two articulated parts (12) connected to each other at a pivot (40) and which each exhibit a handle (14) at one end and at the other end a working end (16) exhibiting a distal end (18) and an inside area (20), such that the inside area (20) has a corrugated portion (24) which runs perpendicular to a longitudinal axis, and a longitudinal groove (26) with a given radius of curvature positioned in the inside area (20), starting at the distal end (18) of the working end (16) and running along the longitudinal axis of the working end (16);

a recessed cavity (30) positioned in a section of the longitudinal groove (26), proceeding from the distal end (18), the radius of curvature of the recessed cavity (30) smaller than the radius of curvature of the rest of the longitudinal groove (26) and a width of the recessed cavity (30) approximately equal to the width of the longitudinal groove (26), whereby the longitudinal groove (26) having at least two different radii of curvature; and at least a part of the corrugated portion (24) extending along the longitudinal groove (26) proximally to the recessed cavity (30).

2. A dental forceps according to claim 1, wherein the radius of curvature of the recessed cavity (30) roughly corresponds to the radius of curvature of a tooth.

3. A dental forceps according to, claim 1, wherein the recessed cavity (30) runs over approximately one third of the length (12) the longitudinal groove (26).

4. A dental forceps according to claim 1, wherein:

the recessed cavity (30) has a transitional area (32) of ellipsoidal shape leading to the longitudinal groove (26); and said part of the corrugated portion (24) extends along the longitudinal groove (26) proximally to the transitional area (32).

5. A dental forceps according to claim 1, wherein the width (b1) the recessed cavity (30) roughly corresponds to the width of a tooth.

6. A dental forceps according to claim 1, wherein the longitudinal edges (34) of the recessed cavity (30) have a cylindrically ground surface exhibiting indentations (38).

7. A dental forceps according to claim 6, wherein the indentations (38) of the ground surface are spaced at a distance of about 1 mm.

8. A dental forceps according to claim 6, wherein approximately two to four indentations (38) are positioned along the recessed cavity (30).

9. A dental forceps according to claim 6, wherein the cylindrically ground surface runs into the recessed cavity (30) at the rim of said recessed cavity (30).

10. A dental forceps according to claim 1, wherein the dental forceps (10) is designed as a stump forceps.

11. A dental forceps according to claim 1, wherein the working end (16) is bent 45 to 90 degrees away from the longitudinal axis of the articulated parts (12).

12. A dental forceps (10) with two articulated parts (12) which are connected to each other at a pivot (40) and which each exhibit a handle (14) at one end and at the other end a working end (16) exhibiting a distal end (18) and an inside area (20), such that the inside area (20) has a corrugated portion (24) which runs perpendicular to a longitudinal axis, and a longitudinal groove (26) with a given radius of curvature positioned in the inside area (20), starting at the distal end (18) of the working end (16) and running along the longitudinal axis of the working end (16); and a recessed cavity (30) positioned in a section of the longitudinal groove (26), proceeding from the distal end (18), the radius of curvature of the recessed cavity (30) smaller than the radius of curvature of the rest of the longitudinal groove (26) and a width of the recessed cavity (30) approximately equal to the width of the longitudinal groove (26), whereby the longitudinal groove (26) having at least two different radii of curvature.

\* \* \* \* \*